US006974820B2

(12) United States Patent
Aberg

(10) Patent No.: US 6,974,820 B2
(45) Date of Patent: Dec. 13, 2005

(54) METHODS FOR TREATING URINARY INCONTINENCE AND OTHER DISORDERS USING TROSPIUM

(75) Inventor: A.K. Gunnar Aberg, Sarasota, FL (US)

(73) Assignee: Bridge Pharma, Inc., Sarasota, FL (US)

( * ) Notice: Subject to any disclaimer, the term of this patent is extended or adjusted under 35 U.S.C. 154(b) by 110 days.

(21) Appl. No.: 10/677,527

(22) Filed: Oct. 2, 2003

(65) Prior Publication Data

US 2005/0043342 A1 Feb. 24, 2005

Related U.S. Application Data

(60) Provisional application No. 60/424,194, filed on Nov. 6, 2002.

(51) Int. Cl.[7] ............................................. A61K 31/44
(52) U.S. Cl. ..................................................... 514/278
(58) Field of Search ........................................ 514/278

(56) References Cited

U.S. PATENT DOCUMENTS

| 3,480,626 | A | | 11/1969 | Pfleger et al. ............ 260/247.2 |
|---|---|---|---|---|
| 5,998,430 | A | | 12/1999 | Schwantes et al. ......... 514/299 |
| 6,482,837 | B1 | | 11/2002 | Wood .......................... 514/315 |
| 2002/0010216 | A1 | * | 1/2002 | Rogosky et al. ............. 514/649 |
| 2003/0144352 | A1 | * | 7/2003 | Cammarata et al. ........ 514/531 |

OTHER PUBLICATIONS

Ulshofer, et al., Clin. Drug Invest. 2001: 21(8): 563–569.*
Pharmacology & Toxicology 1999, 85, 299–304; Svane Beckmann–Knopp et al.; "Inhibitory Effects of Trospium Chloride on Cytochrome P450 Enzymes in Human Liver Microsomes".
Bertholdt H. et al., Arzneimittel–Forsch, 17; 719–726 no date available.
Biochemical Pharmacology, vol. 22, pp. 3099–3108. Pergamon Press, 1973; Yung–Chi Cheng et al.; "Relationship Between the Inhibition Constant (K1) and the Concentration of Inhibitor which causes 50 per cent Inhibition (I50) of an Enzymatic Reaction".
The Lancet; vol. 338; Aug. 10, 1991 pp. 344–345; M.J. Connolly et al.; "Torsades de pointes ventricular tachycardia and terodiline".
Chrysalis; P.a. Gayheart–Walsten, et al.; "Effects of a New Non–Sedating Antihistamine on QTc Interval in a Newly Developed Guinea Pig Model", no date available.
Journal of Cardiovascular Pharmacology; 37: 607–618; 2001; Gary A. Gintant et al.; "The Canine Purkinje Fiber: An In Vitro Model System for Acquired Long QT Syndrome and Drug–Induced Arrhythmogenesis".
Dig Dis 1992; 10: 38–45; Juha M. Gronroos et al.; "Cholinergic Hypothesis of Alcoholic Pancreatitis".

Clinical Pharmacology & Therapeutics Jul. 1996 ; 07019901; pp. 89–98; Kenneth Hartigan–Go, MD et al.; "Stereoselective Cardiotoxic Effects of Terodiline".
Abstracts 487–488; 85A; Hofner et al.; "Tolerability and Efficacy of Trosplum Chloride in a Long–Term Treatment (52 weeks) in Patients with Urge–Syndrome: A Double–Blind, Controlled, Multicentre Clinical Trial", no date available.
Ital Heart J. Suppl. 2000; 1 (3): 419–422; Imperadore et al.; "Arresto cardiaco da fibrillazione ventricolare in corso di pancreatitte acuta biliare: descrizione di un caso clinico e ipotesi eziopatogentiche".
Page from Medscape from WEBMD; Rhythm disorders in gallstones; no date provided, http://intapp.medscape.com/ps/medlineapp/getdoc?ord=1&searchid=15&have–local–holdings–file=1&local__journal–only–O&searchstring–%22arrhythmia%22+and+cholethiasis%22.
British Journal of Pharmacology (2000) 131, 245–254; Stephen E. Jones et al.; "Differences in the effects of urinary incontinence agents S–oxybutynin and terodiline on cardiac K+ currents and action potentials".
The Journal of Pharmacology and Experimental Th rapeutics; vol. 247, No. 3; pp. 867–872; James F. Kachur et al.; "R and S Enantiomers of Oxybutynin: Pharmacological Effects in Guinea Pig Bladder and Intestine", no date provided.
Pharmacology & Toxicology 1998, 82, 161–166; Eeva Lukkari et al.; "Cytochrome P450 Specificity of Metabolism and Interactions of Oxybutynin in Human Liver Microsomes".
British Journal of Urology (1995), 75, 452–456; H. Maderscacher et al.; "Trospium Chloride Versus Oxybutynin: a randomized, double–blind, multicentre trial in the treatment of detrusor hyper–reflexia".
The Journal of Urology; vol. 148, 595–597, Aug. 1992; Charlotte A. Massad et al.; "The Pharmacokinetics of Intravesical and Oral Oxybutynin Chloride".
The Journal of Pharmacology and Experimental Therapeutics; vol. 256, No. 2; L.Noronha–Blob et al.; "Enantiomers of Oxybutynin: In Vitro Pharmacological Characterization at M1, M2 and M3 Muscarinic Receptors and in Vivo Effects on Urinary Bladder Contraction,Mydriasis and Salivary Secretion in Guinea Pigs", no date provided.
Bur J Clin Pharmacol (1994) 47: 337–343; A. Pietzko et al.; "Influences of trospium chloride and oxybutynin on quantitative EEG in healthy volunteers".
Drug Metabolism and Disposition vol. 26, No. 4 pp. 289–293; Hans Postlind et al.; "Tolterodine, A New Muscarinic Receptor Antagonist, Is Metabolized", no date provided.

(Continued)

Primary Examiner—Raymond J. Henley III
(74) Attorney, Agent, or Firm—Nields & Lemack

(57) ABSTRACT

Methods are disclosed using Trospium Chloride, an antimuscarinic smooth muscle relaxant, for the treatment of urinary incontinence, and other disorders, while avoiding the concomitant liability of adverse side effects associated with other antimuscarinic drugs.

28 Claims, No Drawings

OTHER PUBLICATIONS

The Journal of Pharmacology and Experimental Therapeutics; vol. 290, No. 3; pp. 1417–1426; Shuba et al.; "Action Potentials, Contraction, and Membrane Currents in Guinea Pigs Ventricular Preparations Treated with the Antispasmodic Agent Terodiline", no date provided.

Arzneimittel–Forschung/Drug Research 48 (11), 10, 1012–1018 (1998); Smith et al. "Comparison of the Antimuscarinic and Antispasmodic Actions of Racemic Oxybutynin and Desethyloxbutynin and Their Enantiomers with Those of Racemic Terodiline".

Page from Medscape from WEB MD; "Effects of Tolterdoine, Trospium Chloride, and oxybutynin on the central nervous system", no date provided, http://intapp.medscape.com/px/medlineapp/getdoc7ord=4&searchid=3&have_local_holdings_file=1&local_journals_only=0&searchstring=trospium.

Clin Drug Invest 23(6); 395–404, 2003; Diefenbach et al.; "Randomised, Double–Blind Study of the Effects of Oxybutynin, Tolterodine, Trospium Chloride and Placebo on Sleep in Health Young Volunteers".

* cited by examiner

METHODS FOR TREATING URINARY INCONTINENCE AND OTHER DISORDERS USING TROSPIUM

This application claims priority of Provisional Application Ser. No. 60/424,194 filed Nov. 6, 2002, the disclosure of which is hereby incorporated by reference.

FIELD OF THE INVENTION

This invention relates to a compound named Trospium Chloride and having the formula:

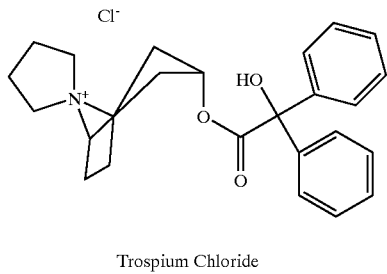

Trospium Chloride

The generic name Trospium Chloride (CAS-10405-02-4; INN) refers to an anticholinergic compound with the chemical name $3_\alpha$-hydroxy-spiro[$1_\alpha$H,$5_\alpha$H-nortropane-8,1'-pyrrolidinium] chloride benzilate; $C_{25}H_{30}ClNO_3$; MW=427.97. In this document, the name trospium refers to Trospium Chloride.

The synthesis of trospium was described by Pfleger R. et al. in U.S. Pat. No. 3,480,626 and by Bertholdt H. et al. in Arzneimittel-Forsch, 1967, 17: 719–726. The preclinical pharmacology and toxicology of trospium was described by Antweiler H. in Arzneimittel-Forsch, 1966, 16:1581–1591.

Trospium may be purchased from Galen Ltd, Craigavon, UK or from Madaus AG, Köln, Germany. Trospium can also be extracted from tablets SPASMOLYT (trospium chloride manufacturer: Hoyer-Madaus, Monheim, Germany) available in Germany, using methods commonly known to those skilled in the art.

Trospium has several known metabolites, the most well known being the spiroalcohol, which is a metabolite formed by ester hydrolysis. The spiroalcohol metabolite has antimuscarinic activity that may contribute to the therapeutic activity of trospium.

Since trospium is a quaternary compound, it does not easily cross the blood-brain barrier and has therefore fewer CNS side effects than oxybutynin (Todorova A., et al., J. Clin. Pharmacol. 2001, 41: 636–644).

Specifically, the present invention relates to the therapeutic use of trospium and the active metabolites thereof, and pharmaceutical compositions containing at least one of said compounds for treating smooth muscle hyperactivity disorders, such as for example urinary disorders, including urinary incontinence and pollakiuria and gastrointestinal disorders, including gastrointestinal hyperactivity, and other smooth muscle hyperactivity or hyperreactivity disorders including those occurring in conjunction with asthma, urolithiasis, cholelithiasis and choledocholithiasis, while avoiding certain serious cardiac side effects of current anticholinergic medication. The risk for such side effects being particularly high in patients with pre-existing Long QT Syndrome and in patients taking medication, such as for example ketoconazole or erthromycin, that through metabolic interaction may increase the risk for QT prolongation by antimuscarinic drugs for urinary urge incontinence, like DITROPAN® (oxybutynin) and DETROL® (tolterodine).

BACKGROUND OF THE INVENTION

Trospium has been shown to reduce bladder hyperactivity in patients suffering from urinary incontinence and exerts spasmolytic effects on the bladder by inhibiting the effects of acetylcholine on smooth muscle. Trospium has selectivity for muscarinic receptors over nicotinic receptors and as a result, no blocking effects are observed at skeletal neuromuscular junctions. Active metabolites of trospium exert antimuscarinic activities that may account for part of the therapeutic activity of trospium.

In particular, compounds within the class of antimuscarinic drugs for urinary incontinence, including terodiline, tolterodine and oxybutynin, cause severe cardiac electrophysiological side effects. These adverse side effects are associated with prolonged QT interval and include but are not limited to ventricular fibrillation and cardiac arrhythmias, such as torsades de pointes. This is the same type of potentially lethal cardiac side effects that led to the withdrawal of several medications from the market; examples of drugs that have been withdrawn of that reason are the antihistamine drug terfenadine, the antihistamine drug astemizole, the prokinetic drug cisapride and the incontinence drug terodiline that is mentioned above.

No known reference teaches or enables the methods of the present invention comprising administering trospium to a human while avoiding said adverse cardiac side effects; nor do the published references alone or in combination suggest these methods.

SUMMARY OF THE INVENTION

Pharmacological studies of trospium have now been performed in comparison with known and marketed antimuscarinic drugs with therapeutic activity against cholinergically mediated diseases, such as for example urinary incontinence. The present studies have confirmed that trospium, as well as terodiline, tolterodine and oxybutynin, have potent antimuscarinic activity.

It has now been found that while the antimuscarinic drugs oxybutynin, tolterodine and terodiline cause a prolongation of the QTc-interval of the ECG, trospium, surprisingly, does not cause this side effect. Prolongation of the QTc interval is highly indicative of risk for a type of fatal cardiac arrhythmias that is called torsades des pointes, as described for the antihistamine terfenadine by Woosley et al. 1993, JAMA 269: 1532–1536 and for the antimuscarinic drug terodiline by Connolly et al. 1991, Lancet 338: 344–345. It is therefore concluded that trospium will offer anticholinergic treatment for muscarinic disorders, including urinary voiding disorders such as urinary urge incontinence and for gastrointestinal disorders, including gastric motility disorders such as diarrhea, while avoiding the concomitant liability of adverse side effects associated with currently used antimuscarinic drugs. Trospium will therefore offer potential for anticholinergic treatment for smooth muscle disorders, including urinary incontinence and gastrointestinal smooth muscle disorders and kidney and gall bladder disorders, while being devoid of the cardiac side effects of the presently used medication.

The fact that no cases of prolonged QTc or no cases of torsades de pointes may have been found in clinical studies of a few thousand patients is irrelevant in the present context, since both prolongation of QTc and Torsades are very rare—but much feared—side effects of drug therapy.

Thus terfenadine (Seldane®) was withdrawn from the market even though this drug caused torsades de pointes arrhythmias in only one out of 200,000 patients and 25 out of 1000 patients may have expressed a significant, drug-induced QTc-prolongation with QTc duration exceeding 440 milliseconds (Morganroth J. pers. communication.)

Trospium is to some degree undergoing hepatic metabolism, resulting in the formation of the spiroalcohol, which is an active (antimuscarinic) metabolite formed by ester hydrolysis. On the contrary, both tolterodine (Postlind et al. Drug Metab Dispos 1998, 26: 289–293) and oxybutynin (Lukkari et al. Pharmacol Toxicol 1998, 82: 161–166) undergo extensive P450-mediated metabolism.

The effects of trospium on CYP 450-induced metabolism of various drugs has been investigated, using human liver microsomes enzymes and drugs that are metabolized by known P450 enzymes. The CYP 2D6-mediated metabolism of 3-[2-NN-diethyl-N-(methyl-ammonium) ethyl]-7-methoxy-4-methyl-coumarin was inhibited by trospium with an IC50 value of about 20 μM, which is significantly higher than the expected therapeutic plasma concentration of trospium that is the range of a few nM. Trospium had even more negligible inhibitory effects on drug metabolism by CYP3A4. As pointed out above, it has been found that tolterodine and oxybutynin potently inhibit both CYP 2D6 and CYP 3A isoenzyme metabolism. Metabolic inhibition of this type is known to increase the concomitant liability of cardiac arrhythmias of drugs that cause QT-prolongation (Woosley et al. JAMA 1993, 269: 1532–1536). The present results demonstrate that trospium will not cause this type of drug interaction. Trospium may therefore be administered together with drugs like ketoconazole, itraconazole or erythromycin without enhanced risk for cardiac arrhythmias caused by QT-prolongation. Trospium can also be used together with antimuscarinic agents like oxybutynin or tolterodine without increased risk for QT-prolongation and such co-administration may preferably substitute for high doses of oxybutynin or tolterodine.

Patients suffering from the disease called Long QT Syndrome should not use medication that may cause further prolongation of the QT-interval of the ECG, but can use trospium without aggravating their pre-existing risk for torsades de pointes cardiac arrhythmias.

Since sudden pain such as the severe and sudden pain in connection with urolithiasis or cholelithiasis, can cause increased risk for cardiac arrhythmias (Ionescu, Drug Metab Dispos 1998, 26: 289–293), trospium will be particularly useful to treat these conditions, since this drug has now been shown not to cause prolongation of the cardiac QT-interval, which would predispose the patient for unwanted cardiac events, like Torsades de pointes ventricular fibrillation. In cases where urgent treatment is preferred, trospium can be administered parenterally and preferentially by the intravenous route to alleviate the smooth muscle spasm and the pain pain in connection with urolithiasis or cholelithiasis.

Since muscarinic receptors have been shown to play a significant role in the etiology of acute pancreatitis (Gronroos et al., Dig Dis 1992, 10: 38–45), trospium will be an ideal drug for the treatment of this disease since pancreatitis is not seldom accompanied by cardiac arrhythmias (Imperadore et al., Ital Heart J. 2000, 1: 419–422.)

Certain individuals are predisposed for cardiac arrhythmias. Thus, individuals suffering from long QT syndrome (LQT) are particularly vulnerable for torsades de pointes arrhythmias. Their risk for lethal torsades de pointes arrhythmias is further increased if these individuals are using medication that further lengthens their cardiac QT interval. However, since trospium has now been shown not to cause QT-prolongation, the risks for torsades de pointes arrhythmias in predisposed patients are not further increased by trospium.

Trospium is a quaternary compound and consequently the drug does not easily pass the blood-brain barrier. It is therefore expected that trospium—contrary to drugs like oxybutynin and tolterodine—will not cause CNS side effects, such as for example memory loss, which is of particular importance in elderly patients (Pietzko A et al. Eur J Clin Pharmacol 1994, 47: 337–343, Todorova A., et al., J. Clin. Pharmacol. 2001, 41: 636–644).

Trospium may cause less pronounced side effects of the types that are typical for antimuscarinic drugs (e.g. dry mouth, blurry vision) and clinical studies have shown this to be the case (Madersbacher H et al., Br J Urol 1995, 75: 452–456 and Hofner K. International Continence Society, Finland, 2000; Abstract Neurourol Urodyn 2000, 19: 487–488). However, antimuscarinic drugs for urinary incontinence are usually given in doses that are as high as possible and side effects such as dry mouth and blurry vision are often the dose-limiting side effect of these drugs.

The magnitude of a prophylactic or therapeutic dose of a compound of the present invention in the acute or chronic management of disease will vary with the severity and nature of the condition to be treated and the route of administration. The dose and the frequency of the dosing will also vary according to the age, body weight and response of the individual patient. Doses as low as 1 mg twice daily to as high as 60 mg twice daily may be administered to patients in need of such therapy. In general, the daily oral dose of trospium is one 20-mg tablet twice daily to patients suffering from urinary urge incontinence. In managing the patient, the therapy may be initiated at a lower dose, perhaps at about 5 mg to about 10 mg, twice daily, and is usually increased up to 20 mg depending on the patient's global response. It is further recommended that patients over 65 years and those with impaired renal or hepatic function initially receive low doses and that they be titrated based on individual response(s) and plasma drug level(s). It may be necessary to use dosages outside these ranges in some cases, as will be apparent to those skilled in the art. Further, it is noted that the clinician or treating physician will know how and when to interrupt, adjust, or terminate therapy in conjunction with individual patient response.

The terms "a therapeutically effective amount" and "an amount sufficient to treat the disorder but insufficient to cause adverse effects" are encompassed by the above-described dosage amounts and dose frequency schedule.

Any suitable route of administration may be employed for providing the patient with an effective dosage of the compounds of the present invention. For example, oral, sublingual, parental (i.e. subcutaneous, intramuscular, intravenous, etc.), transdermal, vaginal, aerosol and like forms of administration may be employed. Additionally, the drug may be administered directly into the bladder, as described for oxybutynin by Massad C. A., et al. J. Urol. 148, 595–597 (1992) and for trospium by Schwantes U., et al. U.S. Pat. No. 5,998,430 or rectally directly into the gastrointestinal canal as known in the art. Dosage forms include tablets, troches, dispersions, suspensions, solutions, capsules, suppositories, microencapsulated systems, slow-release and controlled release systems, transdermal delivery systems, and the like.

Prodrugs of trospium or the spiroalcohol metabolite can be prepared by those skilled in the art, as has been described for an active metabolite of tolterodine by Sparf B. et al. in EP 0957 073 A1. Such prodrugs may offer certain advantages over trospium, such as for example improved bioavailability.

The pharmaceutical compositions of the present invention comprise of trospium or a metabolite thereof as the active ingredient, or any pharmaceutically acceptable salt thereof, and may also contain a pharmaceutically acceptable carrier, and optionally, other therapeutic ingredients.

The terms "pharmaceutically acceptable salts" or "pharmaceutically acceptable salt thereof" refer to salts prepared from pharmaceutically acceptable non-toxic acids. Suitable pharmaceutically acceptable acid addition salts for the compound of the present invention include acetic, benzenesulfonic (besylate), benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pathothenic, phosphoric, p-toluenesulfonic, succinic, sulfuric, tartaric, and the like. The chloride is particularly preferred.

The compositions of the present invention include suspensions, solutions, elixirs or solid dosage forms. Carriers such as starches, sugars, and microcrystalline cellulose, diluents, granulating agents, lubricants, binders, disintegrating agents, and the like are suitable in the case of oral solid preparations (such as powders, capsules, and tablets), and oral solid preparations are preferred over the oral liquid preparations. Because of their ease of administration, tablets and capsules represent the more advantageous oral dosage unit forms, in which case solid pharmaceutical carriers are employed. If desired, tablets may be coated by standard aqueous or nonaqueous techniques.

In addition to the common dosage forms set out above, the compounds of the present invention may also be administered by controlled release means and delivery devices to obtain improved pharmacokinetic profiles (such as sustained and stable plasma levels or prolonged duration of activity) or decreased side effects.

Pharmaceutical compositions of the present invention, suitable for oral administration, may be presented as discrete unit dosage forms such as capsules, cachets, suppositories, or tablets, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation, just as is known for currently marketed antimuscarinic drugs. For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active agent or dispersing agent. Molded tablets may be made by molding, in a suitable machine, a mixture of the powdered compound moistened with an inert liquid diluent. All of the foregoing techniques are well know to persons of skill in the pharmaceutical art. Each tablet may contain from about 5 mg to about 20 mg of the active ingredient. An example of an oral unit dose formulation is shown below.

EXAMPLE 1

Oral Unit Dosage Formulation (Tablets)

| Ingredients | per tablet | per batch of 10,000 tablets |
|---|---|---|
| Trospium | 20 mg | 200 g |
| Microcrystalline cellulose | 30 mg | 300 g |
| Lactose | 70 mg | 700 g |
| Calcium stearate | 2 mg | 20 g |
| FD&C Blue #1 Lake | 0.03 mg | 300 mg |

Trospium is blended with lactose and cellulose until a uniform blend is formed. The lake is added and further blended. Finally, the calcium stearate is blended in, and the resulting mixture is compressed into tablets using, for example, a 9/32 inch (7 mm) shallow concave punch. Tablets of other strengths may be prepared by altering the ration of active ingredient to the excipients or altering the final weight of the tablet.

Pharmacological Studies of Trospium

1. Ligand Binding Studies: Affinity for Muscarinic Receptors.

The experiments were carried out on membranes prepared from SF9 cells that expressed human recombinant muscarinic receptor subtypes. After incubation with the test article and the proper radioligand ($^3$H scopolamine methylchloride) and washing, bound radioactivity was determined with a liquid scintillation counter, using a commercial scintillation cocktail. The specific radioligand binding to a muscarinic receptor was defined as the difference between total binding and nonspecific binding determined in the presence of an excess of unlabelled atropine. $IC_{50}$ values (concentrations required to inhibit 50% of specific binding) were determined by non-linear regression analysis of the competition curves, from which affinity (pKi) values were determined (Cheng Y. et al. Biochem Pharmacol 1073, 22: 3099–3108.)

Results:

Affinity (negative logarithm of the dissociation constant Ki) of trospium and reference compounds for human recombinant receptors

| Test compound | M-1 | M-2 | M-3 | M-4 |
|---|---|---|---|---|
| Trospium | 9.1 | 9.2 | 9.3 | 9.0 |
| Tolterodine | 8.8 | 8.0 | 8.5 | 7.7 |
| Oxybutynin | 8.7 | 7.8 | 8.9 | 8.0 |

Conclusions:

Trospium had slightly higher affinity for human muscarinic receptors than the reference compounds. The therapeutic activity of antimuscarinic drugs in overactive human bladders is generally considered to be related to affinity for M-2/M-3 receptors, while the side effect xerostomia (dry mouth) is due mainly to inhibition of M-1 receptors in salivary glands. (Napier, Gupta)

2. Functional Characterization of Antimuscarinic and Antispasmodic Activities on Bladder Smooth Muscle Strips.

Experiments have now been performed using methods described by Kachur et al, 1988, J Pharmacol Exp Ther 247: 867–872) and Noronha-Blob et al. J Pharmacol Exp Ther 256: 562–567). Strips of tissue (approximately 10 mm long and 1.5 mm wide) were removed from the urinary bladder of male guinea pigs. The tissues were suspended in an oxygenated buffer of the following composition, in mM: NaCl 133; KCl 4.7; CaCl$_2$ 2.5; MgSO$_4$ 0.6; NaH$_2$PO$_4$ 1.3; NaHCO$_3$ 16.3; and glucose 7.7. The smooth muscle strips were maintained at or about 37.5 °C. in tissue chambers and allowed to equilibrate with the bathing solution for one hour before proceeding with the experiment. Contractions induced by carbachol were used to measure anticholinergic actions of trospium and reference compounds (oxybutynin, tolterodine) as described by Smith et al., 1998.

Results:

It has been found that all antimuscarinic compounds tested, potently inhibited carbachol-induced contractions with K$_B$ values between 1.5 nM and 5.5 nM. There were no differences of biological significance between the test compounds, thereby confirming the receptor binding studies in this functional test system.

3. Cardiac Side Effects.

Male or female guinea pigs (450–550 g) were anesthetized with freshly prepared dialurethane sodium. The jugular vein was catheterized for intravenous administration of test drugs and the trachea was exposed and cannulated to facilitate adequate pulmonary ventilation. Transdermal electrodes were positioned for Lead II electrocardiogram recording, monitored on a Grass Recorder, set at a paper speed of 50 mm/sec. The animals were allowed to stabilize for 30 minute after completion of surgery, and three baseline ECG recordings were made at 10-minute intervals. The animals were then given a dose of the test compound or vehicle as an intravenous infusion over 30 min. ECG recordings were used to determine QT intervals and heart rates. To compensate for variations in heart rates, QTc intervals were calculated from QT- and RR-intervals as known to those skilled in the art (Bassett's formula).

Results:

It has now been found that terodiline, oxybutynin and tolterodine, but not trospium, caused statistically significant prolongation of the QTc interval of the ECG from anesthetized guinea pigs.

| Compound | N | ΔQTc (%) |
|---|---|---|
| Vehicle | 8 | −3 ± 1 |
| Terodiline | 8 | +11 ± 1 |
| Oxybutynin | 7 | +12 ± 2 |
| Tolterodine | 7 | +16 ± 1 |
| Trospium | 7 | −2 ± 1 |

Discussion:

The present in vivo test method was introduced by Gayheart-Walsten et al (1998), who demonstrated a significant prolongation of QTc by terfenadine, but not by norastemizole, thereby validating the test method. In the present studies, terodiline also caused significant prolongation of QTc, thereby further validating this in vivo test method.

The present results confirm experimental results of Jones et al. (Br J Pharmacol 2000, 131: 245–254), who found prolongation by terodiline and oxybutynin on action potential duration. Jones et al. (2000) did not test the effects of trospium. Tolterodine prolonged QTc more potently than oxybutynin and terodiline in the present study, but the therapeutic doses of tolterodine are lower than those of oxybutynin and terodiline. There were no effects of trospium or the vehicle on QTc, thereby, surprisingly, demonstrating that trospium can be used as a non-arrhythmogenic antimuscarinic incontinence drug. This is particularly important for a drug like trospium, since it is administered to the patient in a relatively high dose—20 mg at least twice daily. Thus, the compound trospium can even be used by patients who are predisposed for long QT syndrome or patients who may also be taking other drugs that may already cause some QT-prolongation, such as for example erythromycin or ketoconazole.

Prolongation of QTc is indicative of a prolonged cardiac action potential, and is caused by the inhibition of one or more rectifier potassium channels. Prolongation of QTc is the known cause of torsades de pointes ventricular fibrillation by drugs such as terfenadine, astemizole cisapride and terodiline, all of which are now withdrawn from the market because of QTc-prolongation, and—consequently—high risk for lethal torsades de pointes ventricular fibrillation.

It should be pointed out that in vitro electrophysiological studies on the effects of various drugs are considered less predictive than in vivo studies with regard to cardiac events leading to torsades de pointes arrhythmias. Thus, various published studies describe the effects of drugs on action potentials in isolated Purkinje fibers, although the role that the Purkinje fiber action potential plays in the prolongation of the cardiac QT interval is uncertain (Gintant et al. J. Cardiovasc Pharmacol. 2001, 37:608–618.) Numerous in vitro studies have actually been unable to demonstrate the cardiotoxic effects of terfenadine that was withdrawn from the market because of risks for QT-prolongation and Torsades de pointes arrhythmias (for review, see Gintant et al., 2001, page 616.) Similarly, Shuba et al., (3 Pharmacol Exp Ther. 1999, 290: 1417–1426), reported that terodiline in an in vitro study actually shortened the action potential in a dose-dependent manner, although that drug was also withdrawn because it caused lengthening of the cardiac action potential (QT-prolongation) and torsades de pointes in vivo in patients (Hartigan-Go et al., Clin Pharmacol Ther. 1996, 60: 89–98.) The validity of the present in vivo test methodology is evident from the fact that both terfenadine and terodiline caused QT-prolongation in the present studies as the same drugs have been shown to do in vivo in humans Equivalents Those skilled in the art will recognize, or be able to ascertain, using no more than routine experimentation, many equivalents to the specific embodiments of the invention described herein. Such equivalents include numerous pharmaceutically acceptable salt forms e.g. sulfate, fumarate, hydrobromide, hydrochloride, dihydrochloride, methanesulphonate, hydroxynaphthoate, chlorotheophylline or where appropriate one or other of the hydrate forms thereof, see Merck Index 11th edition (1989) items 9089, 209, 3927, 4628, 8223, 5053, 5836, 8142, 2347, 7765, 1840, 9720, 7461, 1317, 4159, and 963 and references cited therein and Am. Rev. Resp. Dis. 1988, 137: (4;2/2) 32. Such equivalents also include the co-administration of at least one compound of the present invention with any other drug that is used to combat diseases in mammals, mentioned in this document. Such equivalents also include the co-administration of at least one compound of the present invention with any other compound or drug that may be used in combination with medication for urinary incontinence or intestinal hyperactivity. Those skilled in the art of medicine will also realize that higher or lower doses than those indicated here may be preferred and the doses may be given more or less frequently than suggested here.

The spiroalcohol metabolite of trospium has antimuscarinic activity and is therefore expected to have therapeutic activity in patients suffering from conditions of smooth muscle hyperactivity. All active metabolites of trospium are included in this present invention.

Those skilled in the art, will realize that smooth muscle motility disorders include disorders of the gastrointestinal tract, including diarrhea and irritable bowel syndromes (IBS) and disorders of the urinary ducts (e.g. "kidney stone pain"; urolithiasis) and the gall fluid ducts (e.g. "gall stone pains"; cholelithiasis and choledocholithiasis) and disorders of the smooth muscle of the airways (e.g. asthma, COPD and bronchitis).

Those skilled in the art of zoophysiology or veterinary medicine will realize that mammals, others than humans, may suffer from smooth muscle disorders, such as urinary incontinence, as well as pancreatitis and pain originating from kidney stones (urolithiasis) or gallstones (cholelithiasis).

Those skilled in the art of pharmacology, will realize that the compounds of the invention, having certain pharmacological properties (such as antimuscarinic activity on various receptor types, calcium antagonistic activity, spasmolytic activity on various types of smooth muscle etc.) may be useful for other indications than those listed here. Such indications include but are not limited to cardiovascular indications such as heart failure, myocardial infarction and stroke, and are equivalents to the specific embodiments of the present invention.

All equivalents are intended to be included in this present invention.

What is claimed is:

1. A method for treating smooth muscle disorders in a mammal suffering from cardiac ventricular arrhythmias or having a propensity for cardiac ventricular arrhythmias, comprising administering to said mammal a therapeutically effective amount of trospium or a pharmaceutically acceptable salt or a metabolite thereof.

2. The method of claim 1; wherein said smooth muscle disorder is a voiding disorder.

3. The method of claim 2, wherein said voiding disorder is a urinary voiding disorder.

4. The method of claim 3, wherein said urinary voiding disorder is urinary urge incontinence.

5. The method of claim 1, wherein said mammal is a human.

6. The method of claim 1, wherein said metabolite is a spiroalcohol metabolite.

7. The method of claim 1, wherein the amount of trospium administered is from 1 mg to 240 mg per day.

8. The method of claim 1, wherein the amount of trospium administered is from 10 mg to 60 mg per day.

9. The method of claim 1, wherein the amount of trospium or a pharmaceutically acceptable salt or metabolite thereof is administered together with a pharmaceutically acceptable carrier.

10. The method of claim 1, wherein said propensity for cardiac ventricular arrhythmia is manifested as a prolonged QT interval of the electrocardiogram of said mammal.

11. The method of claim 1, wherein said cardiac ventricular arrhythmia is torsades de pointes.

12. A method for treating acute pancreatitis in a mammal suffering therefrom, comprising administering to said mammal a therapeutically effective amount of trospium or a pharmaceutically acceptable salt or a metabolite thereof.

13. The method of claim 12 wherein said mammal is a mammal suffering from or having a propensity for cardiac ventricular arrhythmias.

14. The method of claim 13, wherein the propensity for cardiac ventricular arrhythmia is manifested as a prolonged QT interval of the electrocardiogram of said mammal.

15. A method for treating a disorder belonging to the group consisting of urolithiasis and cholelithiasis and choledocholithiasis in a mammal suffering therefrom, comprising administering to said mammal a therapeutically effective amount of trospium or a pharmaceutically acceptable salt or metabolite thereof.

16. The method of claim 15 wherein said mammal is a mammal suffering from or having a propensity for cardiac ventricular arrhythmias.

17. The method of claim 11, wherein the propensity for cardiac ventricular arrhythmia is manifested as a prolonged QT interval of the electrocardiogram of said mammal.

18. A method for treating smooth muscle hyperactivity in a mammal suffering from Long QT Syndrome, comprising administering to said mammal a therapeutically effective amount of trospium or a pharmaceutically acceptable salt or metabolite thereof.

19. A method for treating smooth muscle hyperactivity in a mammal predisposed to cardiac arrhythmias, comprising administering to said mammal a therapeutically effective amount of trospium or a pharmaceutically acceptable salt or metabolite thereof.

20. The method of claim 19 wherein said predisposition is caused by a drug that may cause prolongation of the QT interval.

21. The method of claim 20, wherein said drug that may cause prolongation of the QT interval is selected from the group consisting of oxybutynin and tolterodine.

22. A method for treating smooth muscle disorders in a mammal, comprising determining whether said mammal suffers from or has a propensity for cardiac ventricular arrhythmias, and if said determination is positive, administering to said mammal a therapeutically effective amount of trospium or a pharmaceutically acceptable salt or metabolite thereof.

23. The method of claim 22, wherein said mammal is a human.

24. The method of claim 22, wherein said smooth muscle disorder is a voiding disorder.

25. The method of claim 24, wherein said voiding disorder is a urinary voiding disorder.

26. The method of claim 24, wherein said urinary voiding disorder is urinary urge incontinence.

27. The method of claim 22, wherein said propensity for cardiac ventricular arrhythmia is manifested as a prolonged QT interval of the electrocardiogram of said mammal.

28. The method of claim 22, wherein said cardiac ventricular arrhythmia is Torsades de pointes.

* * * * *